United States Patent [19]

Jurgec et al.

[11] Patent Number: 4,609,731
[45] Date of Patent: Sep. 2, 1986

[54] PROCESS FOR BROMINATING ERGOT ALKALOIDS

[75] Inventors: Milan Jurgec; Rudolf Rucman, both of Ljubljana; Branko Stanovnik, Vrhnika; Miha Tisler, Ljubljana, all of Yugoslavia

[73] Assignee: Sandoz Ltd., Basel, Switzerland

[21] Appl. No.: 141,304

[22] Filed: Apr. 18, 1980

Related U.S. Application Data

[63] Continuation-in-part of Ser. No. 78,978, Oct. 10, 1979, abandoned.

[51] Int. Cl.[4] .................. C07D 457/04; C07D 457/06
[52] U.S. Cl. ..................................... 544/346; 546/69; 544/236
[58] Field of Search ................. 546/69; 544/346, 236; 260/694

[56] References Cited

U.S. PATENT DOCUMENTS 4,076,715  2/1978  Fehr et al. ........................... 544/346
4,219,555  8/1980  Rucman et al. ..................... 424/250

OTHER PUBLICATIONS

Kobe et al.; Tetrahedron, vol. 24, pp. 239–245 (1968).

*Primary Examiner*—Alton D. Rollins
*Attorney, Agent, or Firm*—Gerald D. Sharkin; Robert S. Honor; Thomas O. McGovern

[57] ABSTRACT

The present invention provides an improved process for the production of a compound of formula I

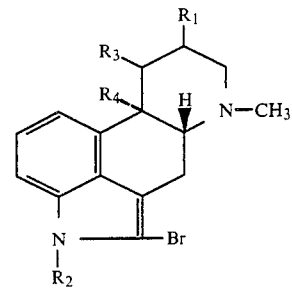

wherein
$R_1$ is carboxyl, alkoxy($C_{1-5}$)carbonyl, amido, alkyl(-$C_{1-5}$)amido, di(alkyl($C_{1-5}$))amido or an amido radical of formula II

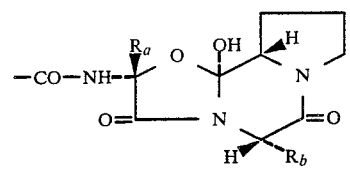

wherein
$R_a$ is alkyl($C_{1-4}$),
$R_b$ is alkyl($C_{1-4}$) or benzyl, and
$R_2$ is hydrogen or alkyl($C_{1-4}$), and
either
$R_3$ is hydrogen and $R_4$ is hydrogen or alkoxy($C_{1-4}$)
or
$R_3$ and $R_4$ together are a single bond,
characterized in that a compound of formula III

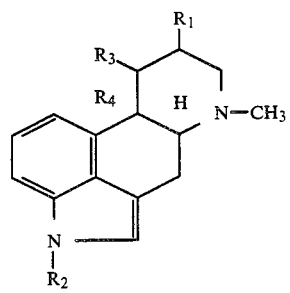

wherein
$R_1$ to $R_4$ are as defined above,
is brominated with a bromine complex of 3-bromo-6-chloro-2-methyl-imidazo[1,2-b]pyridazine.

10 Claims, No Drawings

PROCESS FOR BROMINATING ERGOT ALKALOIDS

This is a continuation in part of our copending application Ser. No. 78,978 filed Oct. 10, 1979, now abandoned.

The present invention relates to brominating processes, especially for selectively brominating sensitive compounds such as ergot alkaloids, e.g. α-ergocryptine.

It is known to brominate α-ergocryptine with a mild brominating agent, e.g. N-bromosuccinimide, N-bromocaprolactam, N-bromophthalamide and bromine/dioxane [see Swiss Pat. No. 507249]. It has also been recently proposed to brominate α-ergocryptine using pyrrolidone-(2)-hydrotribromide or N-bromosaccharin in the presence of a radical initiator (German Offenlegungsschrift No. 2752532).

The present invention provides an novel and advantageous process for the production of a compound of formula I

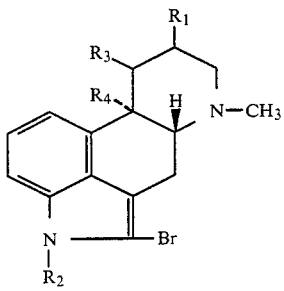

wherein
$R_1$ is carboxyl, alkoxy($C_{1-5}$)carbonyl, amido, alkyl(-$C_{1-5}$)amido, di(alkyl($C_{1-5}$))amido or an amido radical of formula II

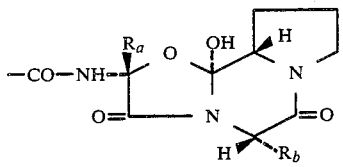

wherein
$R_a$ is alkyl($C_{1-4}$),
$R_b$ is alkyl($C_{1-4}$) or benzyl, and
$R_2$ is hydrogen or alkyl($C_{1-4}$), and
either
$R_3$ is hydrogen and $R_4$ is hydrogen or alkoxy($C_{1-4}$)
or
$R_3$ and $R_4$ together are a single bond,
characterised in that a compound of formula III

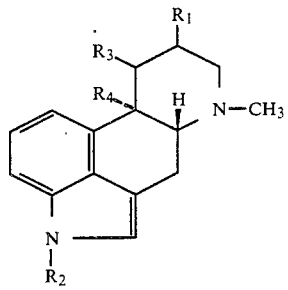

wherein
$R_1$ to $R_4$ are as defined above,
is brominated with a bromine complex of 3-bromo-6-chloro-2-methyl-imidazo[1,2-b]pyridazine.

This brominating agent may for example be prepared by reacting 3-bromo-6-chloro-2-methyl-imidazo[1,2-b]pyridazine or 6-chloro-2-methyl-imidazo[1,2-b]pyridazine with excess bromine. The product is believed to comprise 3-bromo-6-chloro-2-methyl-imidazo[1,2-b]pyridazine dibromide of formula IV

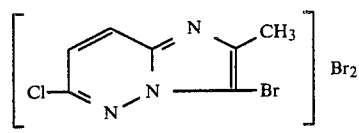

The brominating agent possesses especially advantageous properties. For example it is selective and does not lead to large amounts of side products; it is soluble in a wide range of organic solvents e.g. halogenated solvents and is stable in solution; excess brominating agent may be easily destroyed and the brominated product can be easily separated from the reaction mixture. The brominating agent may be easily regenerated from 3-bromo-6-chloro-2-methyl-imidazo[1,2-b]pyridazine formed in the reaction.

In formulae I and III the side chain in the 8 position may have the α or preferably the β configuration. The brominating reaction proceeds stereospecifically in that epimerisation at the 8 position may be unexpectedly minimal.

For the above mentioned ergot alkaloids, it is preferred to use a ratio of 1 mole of ergot alkaloid to 1.2 to 1.5 moles of brominating agent (based on structure IV). The brominating reaction is preferably effected using methylene chloride or another appropriate chlorinated alkane($C_{1-3}$) as solvent. Suitable reaction temperatures are for example from about −10° C. to about 100° C. At room temperature e.g. 15° to 30° C. satisfactory yields may be surprisingly obtained, for example in a few minutes.

Any excess brominating agent in the reaction mixture may be deactivated by the addition, for example, of acetone and ammonium hydroxide. The isolation of the brominated product is then facilitated. Conventional isolation methods may be used, for example, liquid/liquid extraction and column chromatography, to obtain the brominated product in pure form.

From the reaction mixture 3-bromo-6-chloro-2-methylimidazo[1,2-b]pyridazine may be isolated. This may be converted back into the brominating agent by treatment with excess bromine in concentrated acetic acid.

The brominating agent may be initially produced by reacting 3-bromo-6-chloro-2-methyl-imidazo[1,2-b]pyridazine or 6-chloro-2-methyl-imidazo[1,2-b]pyridazine with excess bromine is concentrated acetic acid, and collecting the resultant precipitate.

The bromination of 6-chloro-2-methyl-imidazo[1,2-b]pyridazine has been described by Kobe et al Tetrahedron, 24, 239 (1968), but there is no indication therein that the bromine complex formed could be used as a brominating agent. 3-bromo-6-chloro-2-methyl-imidazo[1,2-b]pyridazine may be prepared as described in the above-mentioned Tetrahedron article and may be brominated in analogous manner to the bromination of 6-chloro-2-methyl-imidazo[1,2-b]pyridazine and the bromine complex purified in conventional manner. The yield of brominating agent may be conveniently increased by brominating any unreacted starting material in the bromine complex.

The complex may be purified further by crystallization from acetic acid, washing the crystals with ether and drying, e.g. at 30 degrees Centigrade in a vacuum. The complex may contain further bromine over that represented by structure IV, e.g. in the form of HBr.

In the following examples all temperatures are in degrees Centigrade and are uncorrected.

EXAMPLE 1

2-bromo-9,10-dihydroergotamine 0.584 g (1 mMol) 9,10-dihydroergotamine are dissolved in 20 ml methylene chloride. The solution is stirred and 0.612 g (1.5 m Mol) 3-bromo-6-chloro-2-methyl-imidazo[1,2-b]pyridazine-dibromide in 180 ml methylene chloride are added. After the mixture has been stirred for 2 minutes at room temperature, 10 ml acetone and 100 ml 2% aqueous ammonium hydroxide are added. The methylene chloride phase is separated off and the aqueous phase is extracted twice with 200 ml portions of methylene chloride. The combined methylene chloride extracts are concentrated to give a dry residue.

This residue is applied to a column containing 50 g of silicagel. Using an eluant of methylene chloride containing 5% ethanol 0.23 g 3-bromo-6-chloro-2-methyl-imidazo[1,2-b]pyridazine are eluted.

Further elution yields pure 2-bromo-9,10-dihydroergotamine; 0.33 g; 50% yield. M.Pt. 198°–200° and $[\alpha]_D^{20}$ −84° (c=1, pyridine).

Replacing the 9,10-dihydroergotamine with an equivalent amount of:
(a) α-ergosine;
(b) 9,10-dihydro-α-ergosine;
(c) α-ergocryptine;
(d) α-ergosinine;
(e) (5R,8R)lysergic acid diethylamide; or
(f) 1-methyl-9,10-dihydrolysergic acid methyl ester
there are obtained, respectively:
(a) 2-bromo-α-ergosine; 81% yield, M.pt. 183°–185° (decomp) $[\alpha]_D^{20}$= −91.6°, (c=1, chloroform);
(b) 2-bromo-9,10-dihydroergosine; 69% yield, M.pt. 186°–188° (decomp) $[\alpha]_D^{20}$= −40° (c=1, methanol);
(c) 2-bromo-α-ergocryptine; 75% yield, M.pt. 215°–218° $[\alpha]_D^{20}$= −98°; (c=1, pyridine); $[\alpha]_D^{20}$= −195°; (c=1, methylene chloride);
(d) 2-bromo-α-ergosinine; 70% yield, M.pt. 188°–190°; $[\alpha]_D^{20}$= +403°; (c=1, chloroform);
(e) (5R,8R)2-bromo-lysergic acid diethyl amide; 73.4% yield after recrystallization from ether of the dry residue before chromatography, M.pt. 122°–125°; $[\alpha]_D^{20}$= +17° (c=1, pyridine);
(f) 2-bromo-1-methyl-9,10-dihydrolysergic acid methyl ester; 65% yield after recrystallization of the dry residue before chromatography from methanol/water (85:15 by volume), M.pt. 166°–168°; $[\alpha]_D^{20}$= −94° (c=0.5, chloroform).

EXAMPLE 2

Regeneration of 3-bromo-6-chloro-2-methyl-imidazo[1,2-b]pyridazine dibromide 0.23 g (0.93 mMol) 3-bromo-6-chloro-2-methyl-imidazo[1,2-b]pyridazine obtained from Example 1 is dissolved in 2 ml concentrated acetic acid and treated with 1.39 mMol elemental bromine. From the reaction mixture crystallizes out after a little while 3-bromo-6-chloro-2-methyl-imidazo[1,2-b]pyridazine dibromide. This is filtered off and dried. Yield 0.38 g, (89.4%), M.pt 217°–220°.

EXAMPLE 3

Preparation of Brominating Agent

A solution of 1.67 g of 6-chloro-2-methylimidazo[1,2-b]pyridazine [prepared as described in B. Stanovnik and M. Tisler, Tetrahedron, 23, 2739 (1967)] in 25 ml glacial acetic acid is treated dropwise with excess bromine at room temperature. The resulting precipitate is filtered off and washed with glacial acetic acid. The crude brominating agent is crystallised from acetic acid and washed with ether to remove acetic acid. The brominating agent is dried in vacuo at 30° for 60 minutes.

What we claim is:

1. An improved process for the production of a compound of formula I

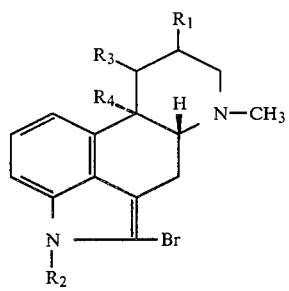

wherein
R₁ is carboxyl, alkoxy($C_{1-5}$)carbonyl, amido, alkyl($C_{1-5}$)amido, di(alkyl($C_{1-5}$))amido or an amido radical of formula II

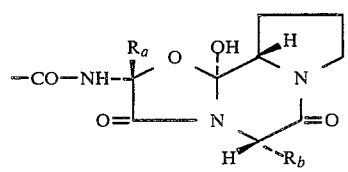

wherein
$R_a$ is alkyl($C_{1-4}$),
$R_b$ is alkyl($C_{1-4}$) or benzyl, and
$R_2$ is hydrogen or alkyl($C_{1-4}$), and
either
$R_3$ is hydrogen and $R_4$ is hydrogen or alkoxy($C_{1-4}$)

or

R₃ and R₄ together are a single bond,
wherein the improvement comprises brominating a compound of formula III

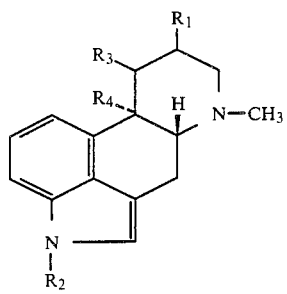

wherein

R₁ to R₄ are as defined above,
with a bromine complex of 3-bromo-6-chloro-2-methyl-imidazo[1,2-b]pyridazine.

2. An improved process according to claim 1 for the production of a compound of formula I wherein the improvement comprises the steps of (a) brominating a compound of formula III as defined in claim 1 with a bromine complex prepared by reacting 3-bromo-6-chloro-2-methyl-imidazo[1,2-b]pyridazine or 6-chloro-2-methyl-imidazo[1,2-b]pyridazine with excess bromine; (b) separating the compound of formula I of step (a) from the 3-bromo-6-chloro-2-methyl-imidazo[1,2-b]pyridazine formed when the desired amount of compound I is produced; (c) forming a bromine complex by reacting the 3-bromo-6-chloro-2-methyl-imidazo[1,2-b]pyridazine of step (b) with excess bromine; and (d) brominating a compound of formula III as defined in claim 1 with the bromine complex of step (c).

3. An improved process according to claim 1 for the production of a compound of formula I wherein the improvement comprises the step of brominating a compound of formula III with a bromine complex prepared by reacting 3-bromo-6-chloro-2-methyl-imidazo[1,2-b]pyridazine or 6-chloro-2-methyl-imidazo[1,2-b]pyridazine with excess bromine.

4. A process according to claim 3 in which the molar ratio of bromine complex to compound of formula III based on a bromine complex structure of the formula

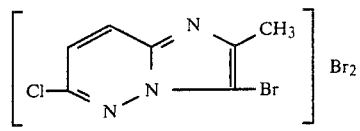

is 1.2 to 1.5 of bromine complex to 1 mole of compound.

5. A process according to claim 3 which is carried out in a chlorinated ($C_{1-3}$)alkane at a temperature $-10°$ C. to $100°$ C.

6. A process according to claim 3 in which the bromine complex is prepared by reacting 3-bromo-6-chloro-2-methylimidazo[1,2-b]pyridazine or 6-chloro-2-methyl-imidazo[1,2-b]pyridazine with excess bromine in concentrated acetic acid and separating the resulting bromine complex precipitate.

7. A process according to claim 3 in which the bromine complex is prepared from 6-chloro-2-methyl-imidazo[1,2-b]pyridazine.

8. A process according to claim 3 in which 3-bromo-6-chloro-2-methyl-imidazo[1,2-b]pyridazine is separated from the compound of formula I when the desired amount of compound is formed.

9. A process according to claim 1 for the production of 2-bromo-α-ergocryptine which comprises the step of brominating α-ergocryptine with a bromine complex of 3-bromo-6-chloro-2-methyl-imidazo[1,2-b]pyridazine.

10. A process according to claim 9 in which α-ergocryptine is brominated with a bromine complex prepared by reacting 3-bromo-6-chloro-2-methyl-imidazo[1,2-b]pyridazine or 6-chloro-2-methyl-imidazo[1,2-b]pyridazine with excess bromine.

* * * * *